United States Patent [19]

Adib

[11] 4,342,086
[45] Jul. 27, 1982

[54] COMPENSATING SYSTEM FOR KINESIOGRAPH MANDIBULAR TRACKER

[75] Inventor: Freydoon Adib, Seattle, Wash.

[73] Assignee: Myo-Tronics, Inc., Seattle, Wash.

[21] Appl. No.: 165,795

[22] Filed: Jul. 3, 1980

[51] Int. Cl.³ .............................................. A61B 5/05
[52] U.S. Cl. ..................................... 364/415; 128/653
[58] Field of Search .................... 364/415; 433/69, 63; 128/653, 777, 782

[56] References Cited

U.S. PATENT DOCUMENTS

| | | | |
|---|---|---|---|
| 3,822,694 | 7/1974 | Mills | 433/69 X |
| 4,083,114 | 4/1978 | Acevendo | 433/63 |
| 4,197,855 | 4/1980 | Lewin | 128/653 |

Primary Examiner—Edward J. Wise
Attorney, Agent, or Firm—Seed, Berry, Vernon & Baynham

[57] ABSTRACT

A system for compensating for geometric distortions inherent in a kinesiograph mandibular tracker which measures mandibular movement using an array of sensors generating respective outputs representing the distances between the sensors and a reference point on the mandible. The kinesiograph mandibular tracker generates approximate position outputs from the sensor outputs which correspond to the approximate vertical, anterior-posterior and lateral position of the reference point. The approximate position outputs are applied to the compensating system which periodically samples and stores the outputs. Each of the stored samples is sequentially digitized and applied to a processing unit. After the digitized signal for each approximate position output has been stored in the processing unit, the processing unit calculates the actual position of the reference point and sequentially generates digitized representations of the actual vertical, anterior-posterior and lateral positions of the reference point. An analog signal is derived from each digitized representation as it is produced, and the analog signals are routed to respective sample-and-hold circuits which continuously generate actual position outputs corresponding to the actual vertical, anterior-posterior and lateral position of the reference point. These actual position outputs are applied to the kinesiograph mandibular device in the same manner that the approximate position outputs are normally applied.

12 Claims, 8 Drawing Figures

COMPENSATING SYSTEM FOR KINESIOGRAPH MANDIBULAR TRACKER

BACKGROUND OF THE INVENTION

1. Field of the Invention

This invention relates to dental instrumentation devices, and more particularly, to a system for allowing the display and recording of mandibular movement with a greater degree of accuracy than has been heretofore possible.

2. Description of the Prior Art

A kinesiograph mandibular tracker is a dental instrument used to measure and record mandibular movement which is sold by Myo-tronics Research, Inc., of Seattle, Wash. The kinesiograph mandibular tracker, which is described and claimed in U.S. Pat. No. 3,822,694, utilizes an array of sensors to measure the position of a magnet affixed to the lower incisors of the patient's mandible. The kinesiograph mandibular tracker uses these sensor outputs to generate signals representing frontal, sagittal and horizontal mandibular movement, and displays these signals on the face of a cathode ray tube. The kinesiograph mandibular tracker thus easily and quickly provides the kind of factual information needed to determine and diagnose occlusal problems.

Although the kinesiograph mandibular tracker has been advantageously used for many years with great success, the accuracy of the displayed position information is nevertheless limited by geometric distortions inherent in the arrangement of the sensor array. The sensors in the array generate outputs which are proportional to the distance between the sensor and the magnet affixed to the patient's mandible. The sensors thus accurately measure movement of the mandible when the mandible is moving directly toward and away from the sensor. However, mandible movements which are not directly toward and away from the sensor are not accurately measured. In other words, the sensors measure the vector component toward and away from the sensors, which differs from the actual movement vector when the vector contains components perpendicular to a line extending between the sensor and the magnet. The accuracy of the device is also affected by pure rotational movements of the magnet which alter the strength of the magnetic field at the sensor and are thus erroneously perceived as movements of the magnet. Another component of distortion is the slight degree of non-parallelism between the flux lines of the magnet and each sensor. Consequently, the conventional kinesiograph mandibular tracker displays approximate, but not actual, mandibular movement.

SUMMARY OF THE INVENTION

It is an object of the invention to provide a compensating system for correcting errors which are inherent in conventional kinesiograph mandibular trackers.

It is another object of the invention to provide a compensating system for a kinesiograph mandibular tracker which may be used without significant internal modification of the kinesiograph mandibular tracker.

It is still another object of the invention to provide a compensating system for a kinesiograph mandibular tracker in which input signals representing the approximate position coordinates of the mandible are processed in synchronism with the generation of output signals representing the actual position coordinates of the mandible to ensure that the coordinates represented by the output signals correspond to the coordinates represented by the input signals.

These and other objects of the invention are provided by a compensating system which calculates the position coordinates corresponding to the actual position of a reference point on a patient's mandible using the same coordinate system as the approximate position coordinates corresponding to uncorrected position signals from the kinesiograph mandibular tracker. Corrected position signals corresponding to the actual position coordinates are then generated which may be applied to the kinesiograph mandibular tracker in the same manner that the corresponding uncorrected position signals are applied to the kinesiograph mandibular tracker. The corrected position signals are thus the corresponding uncorrected position signals which have been corrected for the geometric distortion inherent in the kinesiograph mandibular tracker. The uncorrected position signal is first sampled and stored, and the stored samples are sequentially selected and isolated one at a time by a first multiplexer and then applied to an analog-to-digital convertor which generates a digital word representative of the selected sample. A processing means sequentially stores the digital word for each sample and, after digital words for all of the samples have been received, calculates the actual position coordinates of the reference point using the same coordinate system as the approximate position coordinates. A digital-to-analog convertor then generates an analog corrected position signal for each coordinate, and a second multiplexer applies the analog signals to one of several output lines depending upon which position coordinate the analog signal represents. The first and second multiplexers are preferably operated by common control signals so that they are synchronized to each other. Similarly, the circuits sampling the uncorrected position signals and the corrected position signals, as well as the analog-to-digital convertor and digital-to-analog convertors, are preferably operated by common control signals to allow maximum utilization of limited control lines.

DETAILED DESCRIPTION OF THE INVENTION

Figure 1:
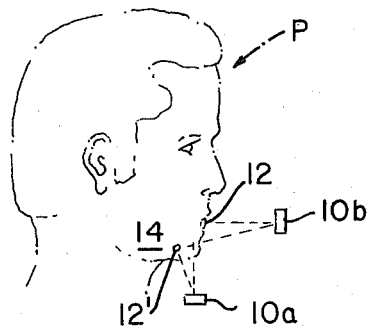
FIG. 1 is a schematic view illustrating the geometric distortions inherent in the kinesiograph mandibular tracker.

A portion of the kinesiograph mandibular tracker having an array of sensors 10 is illustrated in FIG. 1. A magnet 12 is affixed to the mandible 14 of a patient P adjacent the lower incisors. The magnet 12 generates flux lines which are detected by the sensors 10. The sensors 10, by measuring the strength of the magnetic flux, are thus able to measure the distance between the sensors 10 and the magnet 12. However, the distance between the sensors 10 and the magnet 12 provides an indication of the magnet's movement only when the magnet 12 is moving directly toward or away from the sensors 10. As illustrated in FIG. 1, when the magnet 12 initially moves, it moves directly toward the sensor 10a so that the sensor 10a can accurately measure the position of the magnet 12. However, as the mandible opens wider, the magnet 12 no longer moves directly toward the sensor 10a. In fact, in the exaggerated example shown in FIG. 1, the magnet 12' remains a fixed distance from the sensor 10a as it moves. Under these circumstances, the sensor 10a cannot accurately measure the movement of the magnet 12. These geometric distortions are inherent in the operation of the conventional kinesiograph mandibular tracker. In the past, the output of the sensor 10a was considered to represent the vertical movement of the magnet 12 even though the output is affected by the magnet's direction of movement. Consequently, such kinesiograph mandibular trackers have produced acceptable but somewhat erroneous measurements.

Figure 2:
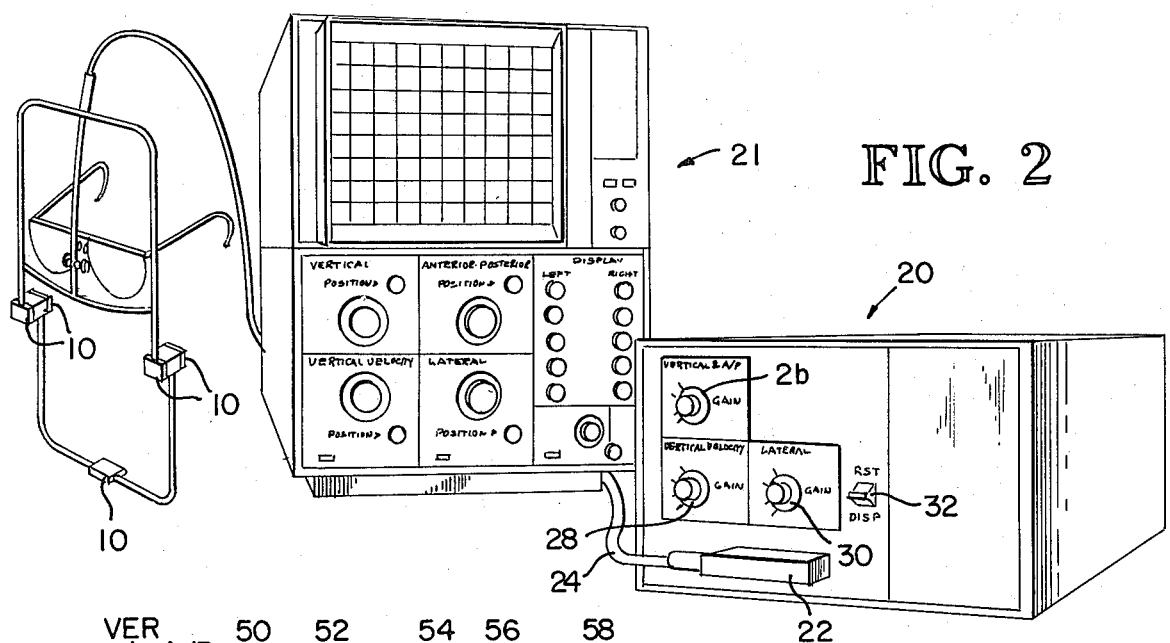
FIG. 2 is an isometric view of the compensating system and the kinesiograph mandibular tracker.

A system for compensating for the geometric distortion inherent in the conventional kinesiograph mandibular tracker is illustrated in FIG. 2. The compensating system 20 is connected to a conventional kinesiograph mandibular tracker 21 through a connector 22 and cable 24. The cable 24 contains leads receiving uncorrected position outputs from the kinesiograph mandibular tracker indicative of the vertical, anterior-posterior and lateral position of the magnet 12. The cable 24 also contains leads applying corrected vertical, anterior-posterior and lateral position signals to the kinesiograph mandibular tracker in the same manner that the uncorrected position signals are utilized.

The front panel of the system 20 includes respective gain controls 26, 28, 30 for adjustably scaling the vertical and anterior-posterior, vertical velocity and lateral position outputs. The system 20 also includes a multipurpose switch 32 which is deflected upwardly to initially reset the system and downwardly to commence processing the uncorrected vertical, anterior-posterior and lateral information, and compensate for the geometric distortion and display the corrected data.

Figure 3:
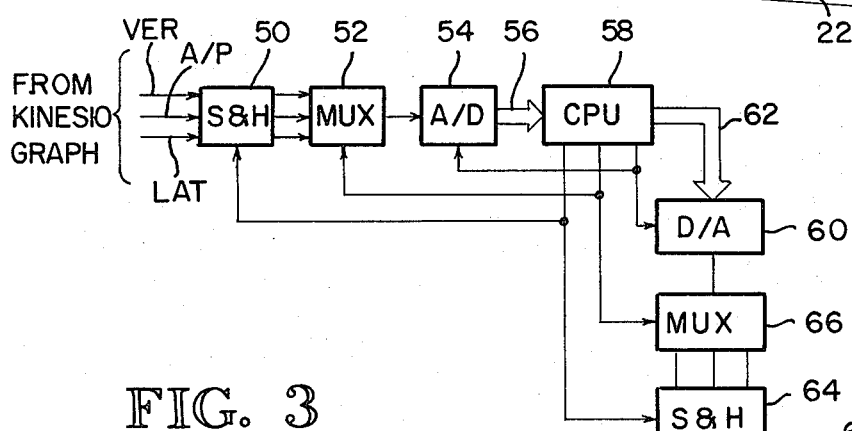
FIG. 3 is a block diagram of the compensating system of FIG. 2.
Figure 3:
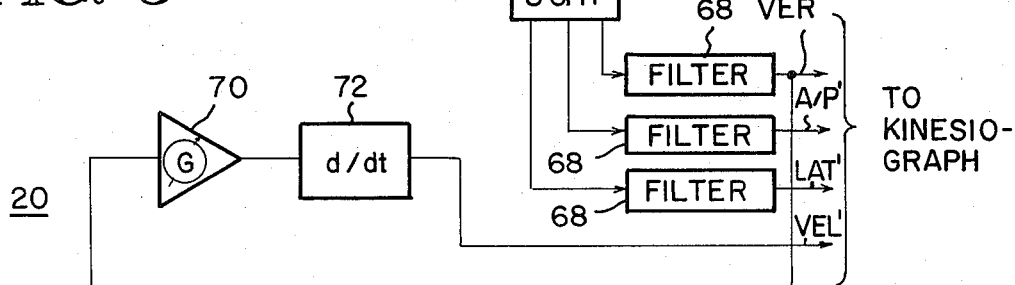
Figure 4A:
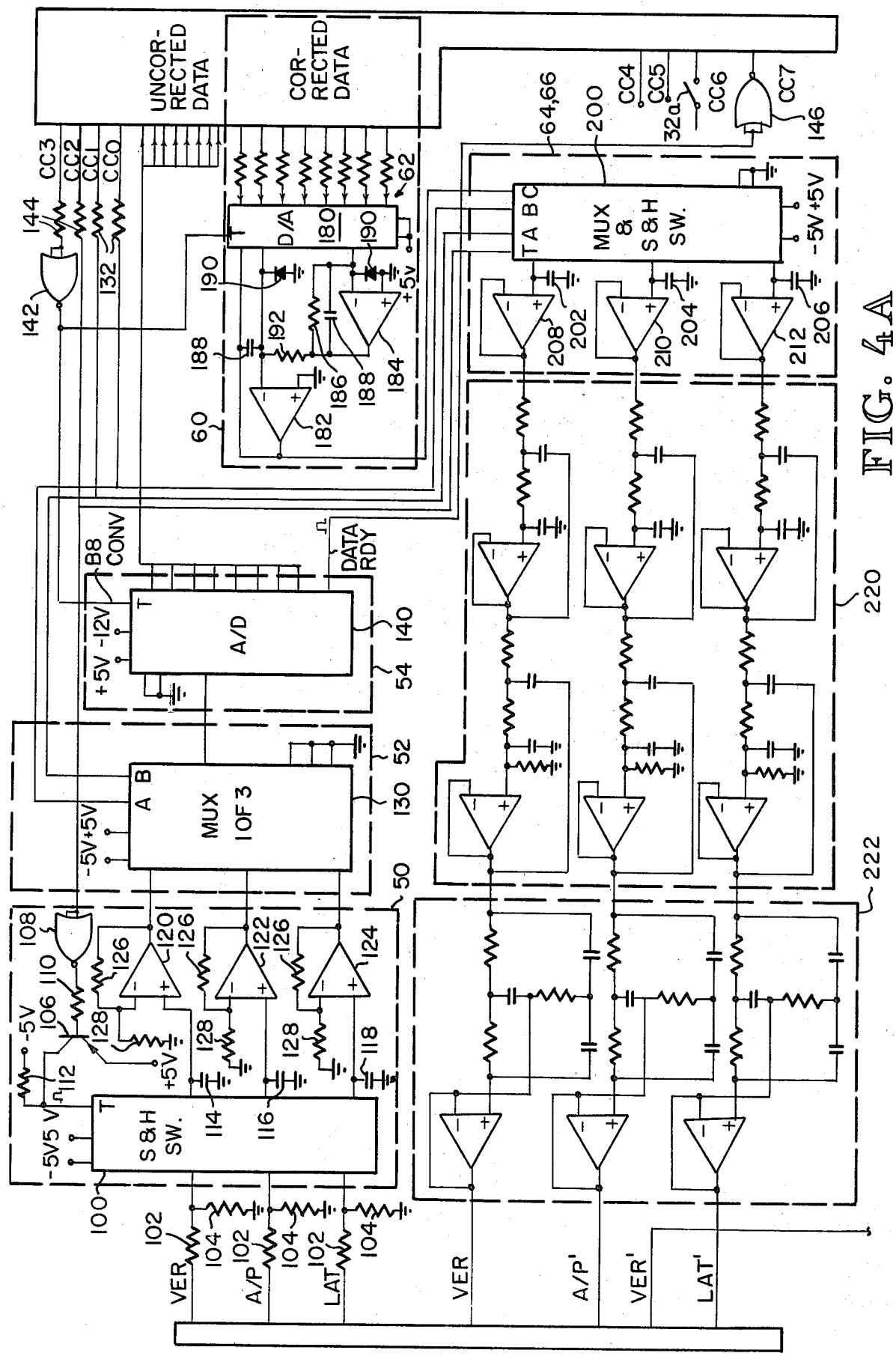
FIGS. 4A-4D are a schematic of the compensating system of FIG. 2.
Figure 4B:
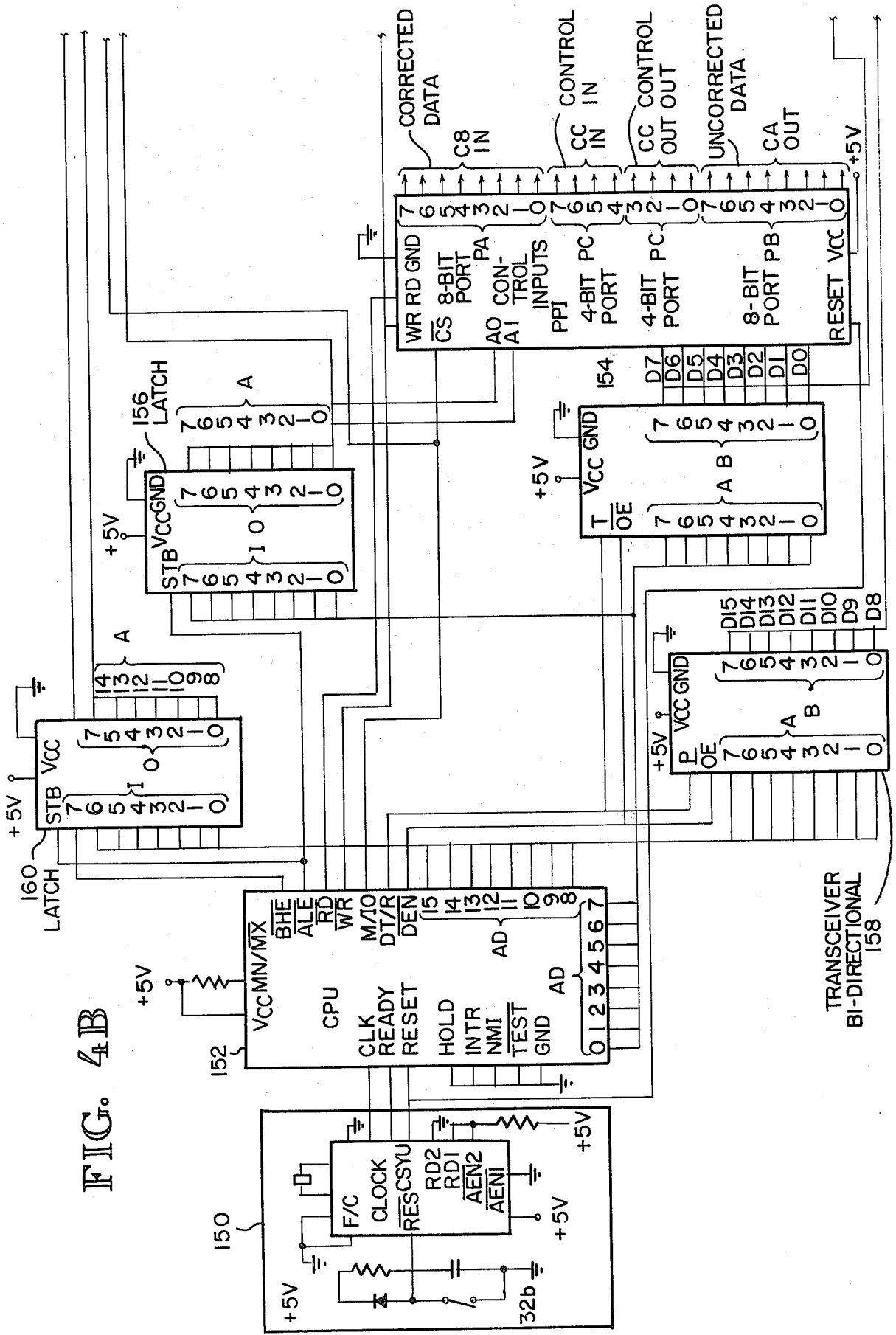
Figure 4C:
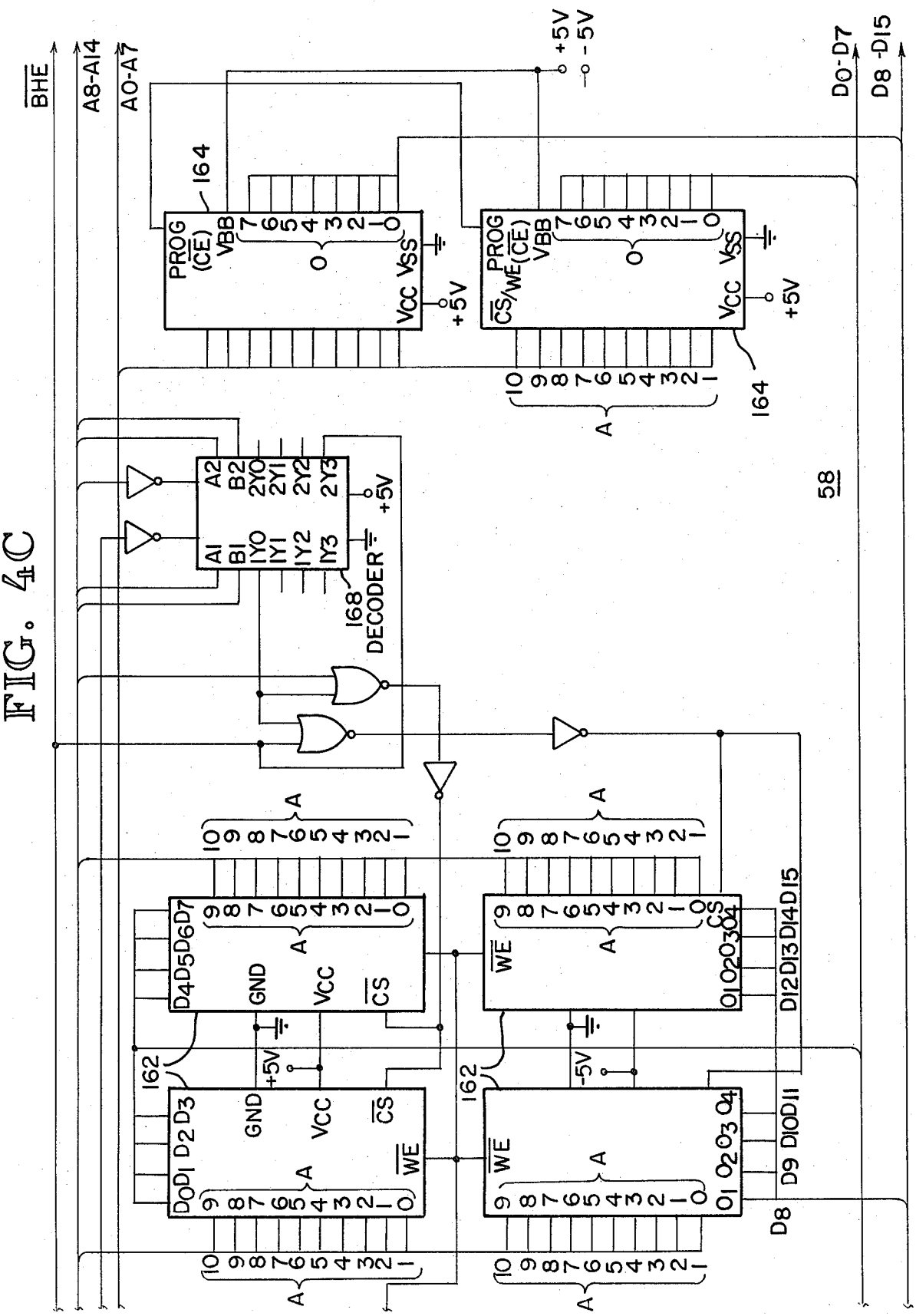
Figure 4D:
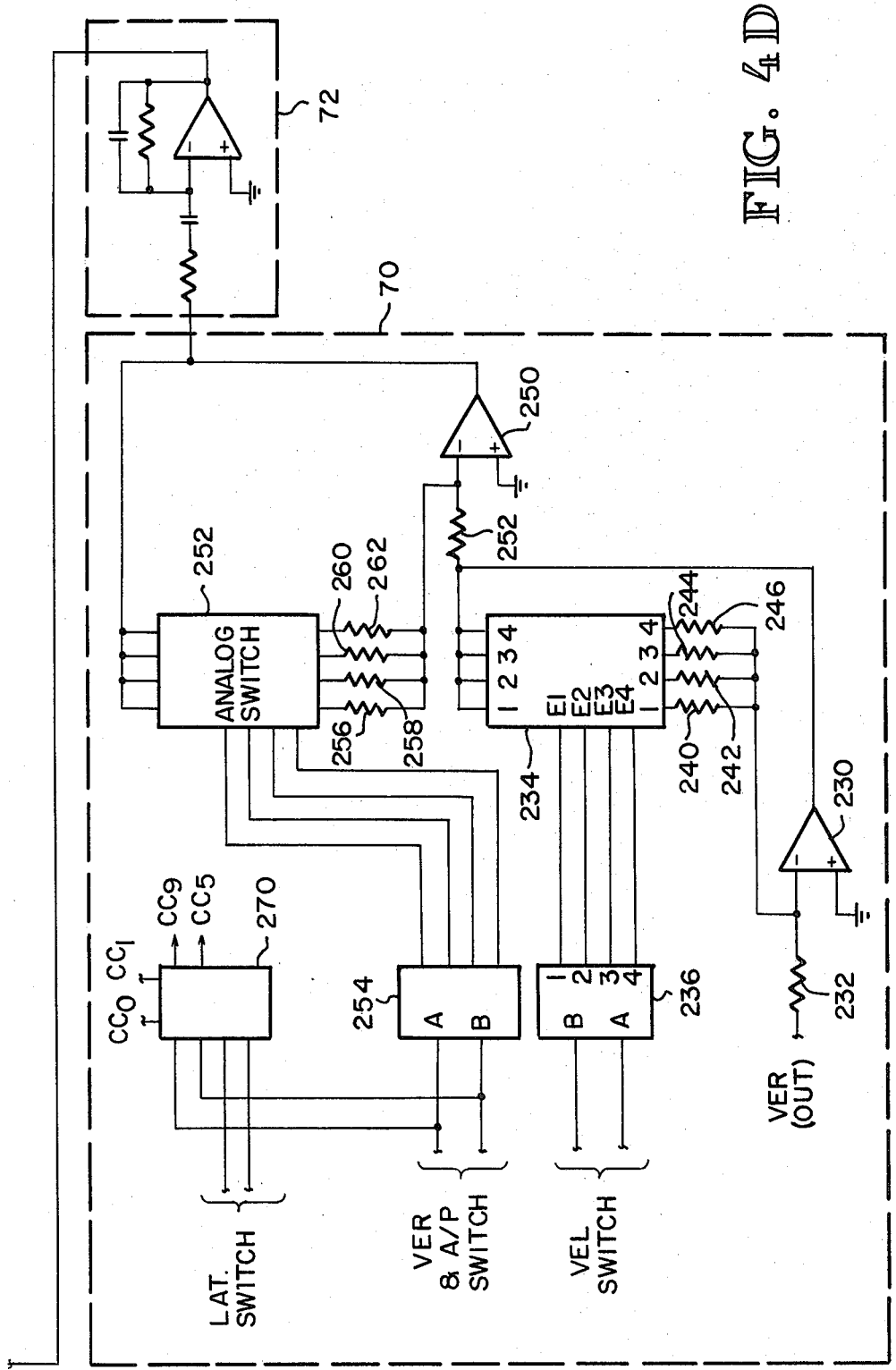

A block diagram of the compensating system 20 is illustrated in FIG. 3. Uncorrected position signals VER, A/P and LAT, representative of the uncorrected vertical, anterior-posterior and lateral position of the magnet 12, are periodically sampled by a sample-and-hold circuit 50. The sampled uncorrected position signals are stored by the circuit 50 and applied to a multiplexer 52. The multiplexer 52 sequentially selects one of its inputs and applies it to an analog-to-digital convertor 54 which generates a binary signal or data word on data bus 56 representing the value of the analog signal from the multiplexer 52. Bus 56 is connected to the data bus of a central processing unit 58 which is preferably a conventional microprocessor device. Thus, the central processing unit 58 sequentially receives digital words representing the uncorrected position signals VER, A/P and LAT. The processing unit 58 utilizes the uncorrected position coordinates to calculate the actual position coordinates of the magnet 12 free of the geometric distortion affecting the uncorrected position signals. Digital words corresponding to these corrected position coordinates are sequentially applied to a digital-to-analog convertor 60 through bus 62. The digital-to-analog convertor 60 generates an analog voltage having a magnitude determined by the value of each data word. The analog voltages are routed to one of three inputs to a sample-and-hold circuit 64 by a second multiplexer 66. Thus, when the central processing unit 58 generates a data word indicative of the actual vertical position of the magnet 12, the corresponding analog signal from the digital-to-analog convertor 60 is routed to the first input to the sample-and-hold 64 by the multiplexer 66. Similarly, the analog signal corresponding to the anterior-posterior position of the magnet 12 is routed to the second input of the sample-and-hold 64 and the analog signal corresponding to the lateral position of the magnet 12 is applied to the third input of the sample-and-hold 64. The sample-and-hold 64 periodically samples these analog signals and continuously applies the samples to respective filters 68 which attenuate their high-frequency and 60-cycle components. The outputs of the filters are thus corrected position signals indicative of the actual coordinates of the magnet 12. These actual position coordinates utilize the same coordinate system (i.e., vertical, anterior-posterior and lateral coordinates) as the uncorrected position inputs to the system 20. Consequently, the outputs of the compensating system 20 may be applied to the kinesiograph device in the same manner that the corresponding inputs to the compensating system 20 are normally applied to the kinesiograph mandibular tracker. Significant internal modification of the kinesiograph mandibular tracker is thus unnecessary.

It will be noted that the sample-and-hold 50 and the sample-and-hold 64 are operated by common control signals, the multiplexer 52 and the multiplexer 66 are operated by common control signals, and the analog-to-digital convertor 54 and digital-to-analog convertor 60 are operated by common control signals. Consequently, each functional block is simultaneously enabled, disabled, or "don't care" switched and eliminates potential timing errors.

A schematic of the compensating system corresponding to the block diagram of FIG. 3 is illustrated in FIGS. 4A-4D. The uncorrected position signals VER, A/P and LAT, corresponding to the vertical, anterior-posterior and lateral positions of the magnet 12, respectively, are applied to a semiconductor switch 100 through respective divider networks formed by resistors 102,104. The switch 100 connects its inputs to respective outputs when a positive-going pulse is applied to its trigger input by transistor 106. The collector of transistor 106 is normally low by virtue of the positive voltage at the output of NOR-gate 108, which is applied to the base of transistor 100 through resistor 110. When a logic "1" is applied to the input of NOR-gate 108, however, transistor 106 turns on, thereby applying the positive trigger voltage to the switch 100.

Actuating the switch 100 applies the uncorrected position signals to respective capacitors 114,116,118 which then store the value of the signals after the switch 100 has opened at the termination of the trigger signal from transistor 106. The voltages are applied to the non-inverting terminals of respective operational amplifiers 120,122,124 having feedback resistors 126 and summing junction resistors 128 which adjust the gain of the amplifiers 120-124 to compensate for the attenuation of the divider resistors 102,104. The amplifiers 120-124 have a high input impedance so that the voltages stored on capacitors 114-118 remain constant between samples. The amplifiers 120-124 thus continuously produce analog signals which are equal to the sampled uncorrected position signals from the kinesiograph mandibular tracker.

The analog signals from the sample-and-hold circuit 50 are then applied to the multiplexer 52, which consists of a conventional one-of-three semiconductor switch 130. The switch applies one of its three inputs to its output depending upon the value of the binary signal at the control inputs A,B, which are generated by the processing unit 58, as explained hereinafter, and connected to the switch 130 through resistors 132. Thus, control inputs A,B of "0,0" apply the output of amplifier 120 to the output of the switch 130, and control inputs A,B of "1,0" apply the output of amplifier 124 to the output of switch 130. The switch 130, forming the multiplexer 52, thus applies one of the outputs of the amplifiers 120,124 to an analog-to-digital convertor 54.

The analog-to-digital convertor 54 is formed by a conventional semiconductor circuit 140 which produces an eight-bit digital word indicative of the value of the received analog signal when a logic "0" is applied to its trigger input from NOR-gate 142. NOR-gate 142 is, in turn, triggered by the processing unit 58 through resistor 144. The analog-to-digital convertor circuit 140 also generates a DATA RDY pulse when the analog input has been digitized. This DATA RDY pulse is applied to the processing unit 58 through a NAND-gate 146, acting as an inverter to inform the unit 58 that a valid output is present at the convertor 140. The data word from the analog-to-digital convertor 54 is applied to the processing unit 58 through the data bus 56, as explained hereinafter.

The central processing unit 58 is of conventional design, including the usual clock circuitry 150 driving a conventional microprocessor circuit 152. The eight low-order address bits are applied to a conventional bidirectional transceiver 154 and to a conventional latch circuit 156. The eight high-order address bits are also applied to a bidirectional transceiver 158 and a second latch 160. The transceivers 154, 158 are used to create a sixteen-bit data bus from the sixteen-bit combination address/data bus of the microprocessing circuit 152. The latch circuits 156,160 are used to create a sixteen-bit address bus from the sixteen-bit combination address/data bus of the microprocessor circuit 152.

In operation, a sixteen-bit address is applied to the latches 156,160 through the combination address/data bus. The latches 156,160 then retain the address and apply it to the address bus. During the next processing cycle, the microprocessor circuit 152 outputs or receives a sixteen-bit data word on the combination address/data bus which is routed through the bidirectional transceivers 154,158. The address buses and data buses are connected to conventional random access memory chips 162 and read-only memory chips 164 containing the program. Chip-enable signals which select one of the random access memory circuits 162 are generated by a conventional chip-decoder circuit 168.

Signals received from and applied to the analog-to-digital convertor 54 and the digital-to-analog convertor 60, respectively, as well as the control signals for the remaining circuitry, are produced by a conventional interface circuit 170. The circuit 170 connects the low-order bits of the address bus to one of three buses, depending upon the value of control inputs $A_0$, $A_1$ selected by two bits of the address. Thus, control inputs of "0,0" connect the data bus to the PA bus of the circuits 170 so that the microprocessing circuit 152 receives data from the analog-to-digital convertor 54 through bus 56. A control input of "0,1" connects the data bus to the PB bus so that the microprocessor 152 can apply corrected position coordinates to the digital-to-analog convertor 60 through bus 62. Finally, control inputs of "1,0" connect the data bus to the PC bus so that signals on the data bus can enable the sample-and-hold circuits 50,64, the multiplexers 52,66 and the analog-to-digital and digital-to-analog convertors 54,60, respectively. The "1,0" control input also allows the microprocessor circuit to receive the DATA RDY pulse from the analog-to-digital convertor and the output from from the occlusion and reset switches 32a,b. The central processing circuit 152 thus sequentially receives eight-bit words representing the uncorrected position coordinates of the magnet 12. Each coordinate is retained in the random access memory 162 until all three coordinates have been received, at which point the processing circuit 152 calculates the actual position coordinates of the magnet 12. Digital words corresponding to each position coordinate are then sequentially applied to the digital-to-analog convertor 60 and routed to the appropriate sample-and-hold 64 by the multiplexer 66.

The digital-to-analog convertor 60 receiving the corrected position coordinates includes a conventional digital-to-analog convertor circuit 180 which is connected with operational amplifiers 182,184 in a conventional manner. Briefly, the circuit 180 includes a feedback resistor and a summing resistor which set the gain of the amplifier 182. The amplifier 184 utilizes an external feedback resistor 186 and a summing resistor that is internal to the circuit 180. Capacitors 188 are used to reduce the high-frequency gain of the amplifiers 182,184 for purposes of stability. Protective diodes 190 are provided to clip negative signals on the inputs the amplifiers 182, 184. Negative values of the position coordinate apply a positive voltage to the non-inverting terminal of amplifier 182 so that the digital-to-analog convertor 60 produces a negative output. Positive position coordinates apply a positive voltage to the inverting terminal of amplifier 184 so that amplifier 184 applies a corresponding negative voltage to the inverting input of amplifier 182 through resistor 192. This negative voltage is once again inverted by amplifier 182 so that the digital-to-analog convertor 60 produces a positive voltage. The digital-to-analog convertor produces the analog outputs only when a logic "0" signal is applied to its trigger input from NOR-gate 142.

The output of the digital-to-analog convertor 60 is applied to a conventional semiconductor switch 200. The switch 200 connects its input to one of three outputs when a logic "1" pulse is applied to its trigger input. The particular output selected is determined by the value of control inputs A, B and C. Thus a control input of "100" connects the output of the digital-to-analog convertor 60 to the first output of switch 200. A control input of "101" connects the output of convertor 60 to the second output of switch 200. A control input of "110" connects the output of convertor 60 to the third output of switch 200. The outputs of the switch 200 are applied to respective storage capacitors 202,204,206. Thus, when the switch 200 is enabled, the analog voltage from the digital-to-analog convertor 60 is applied to one of the capacitors 202–206 which retains that voltage and continuously applies it to respective voltage-follower amplifiers 208,210,212.

In operation, the convertor 60 sequentially produces analog signals corresponding to the corrected position coordinates of the magnet 12, and these analog signals are stored by capacitors 202–206 and continuously presented at the output of amplifiers 208–212. The switch 200, capacitors 202–206 and amplifiers 208–212 thus function as both a multiplexer and a sample-and-hold circuit, and they correspond to the multiplexer 66 and sample-and-hold 64 of FIG. 3.

The outputs of the amplifiers 208-212 are applied by the amplifiers 208-212 to the filter circuits 68, which include respective low-pass, fourth order, Butterworth filters 220 having a 250 Hz break-point and a 60 Hz notch filter 222. Both of these filters 220, 222 are of conventional design and are thus not explained in detail herein. The low-pass filter 220 removes switching transients and high-frequency noise signals from the output of the sample-and-hold 64, while the 60 Hz notch filter 222 removes 60-cycle hum from the output of the compensating unit. The outputs of the filters 222 are thus analog voltages corresponding in scale and identity to the uncorrected position coordinates entering the system. They are, in fact, equal to their respective inputs, corrected for the geometric distortion inherent in the conventional kinesiograph mandibular tracker.

The compensating system 12 also utilizes the corrected vertical position signal VER to generate a signal proportional to the vertical velocity of the magnet 12. Accordingly, the VER signal is applied to an operational amplifier 230 through a summing resistor 232. The feedback resistance for the amplifier 230 is selected by a conventional switch 234. The switch 234 is, in turn, controlled by a multiplexer circuit 236. The multiplexer circuit 236 generates a logic "1" at the output terminal determined by the signal at its control inputs A,B. Thus, a logic "0,0" control input signal produces a logic "1" at the first output terminal, while a "1,1" control input produces a "1" at the fourth output terminal. The switch 234 connects correspondingly positioned lines to each other when the switch is enabled by the correspondingly positioned control inputs. Thus the first terminals are interconnected when a logic "1" is applied to the $E_1$ terminal, thereby placing resistor 240 in the feedback circuit of amplifier 230. In a similar manner, the control inputs to the multiplexer 236 select resistors 242, 244 or 246 for connection in the feedback circuit of amplifier 230. The control inputs to the switch 236 are generated directly by a conventional encoder (not shown) which is actuated by the vertical gain control 26 (FIG. 2).

The output of amplifier 230 is applied to a second operational amplifier 250 through summing resistor 252. The gain of amplifier 250 is controlled in the same manner as amplifier 230 utilizing a second switch 252 which is controlled by a multiplexer 254 in the same manner that the multiplexer 236 controls switch 234. Resistors 256, 258, 260, 262 are thus connected in the feedback circuit of amplifier 250, depending upon the value of the control inputs to multiplex circuit 254 which are directly controlled by the vertical and anterior-posterior gain adjustment 26 (FIG. 2). Both the vertical and A/P gain control signals and the lateral gain control signals from adjuster 30 are also applied to a multiplexer 270 and are selectively connected to the processing unit 58 by control signals connected to A,B terminals, which also emanate from the processing unit 58. The processing unit reads the positions of the vertical and anterior-posterior gain adjustment 26 and lateral gain adjustment 30 by generating appropriate control outputs. The velocity gain signals are not applied to the processing unit since the velocity output is generated by the corrected vertical position signal independently of the processing unit.

Figure 5:
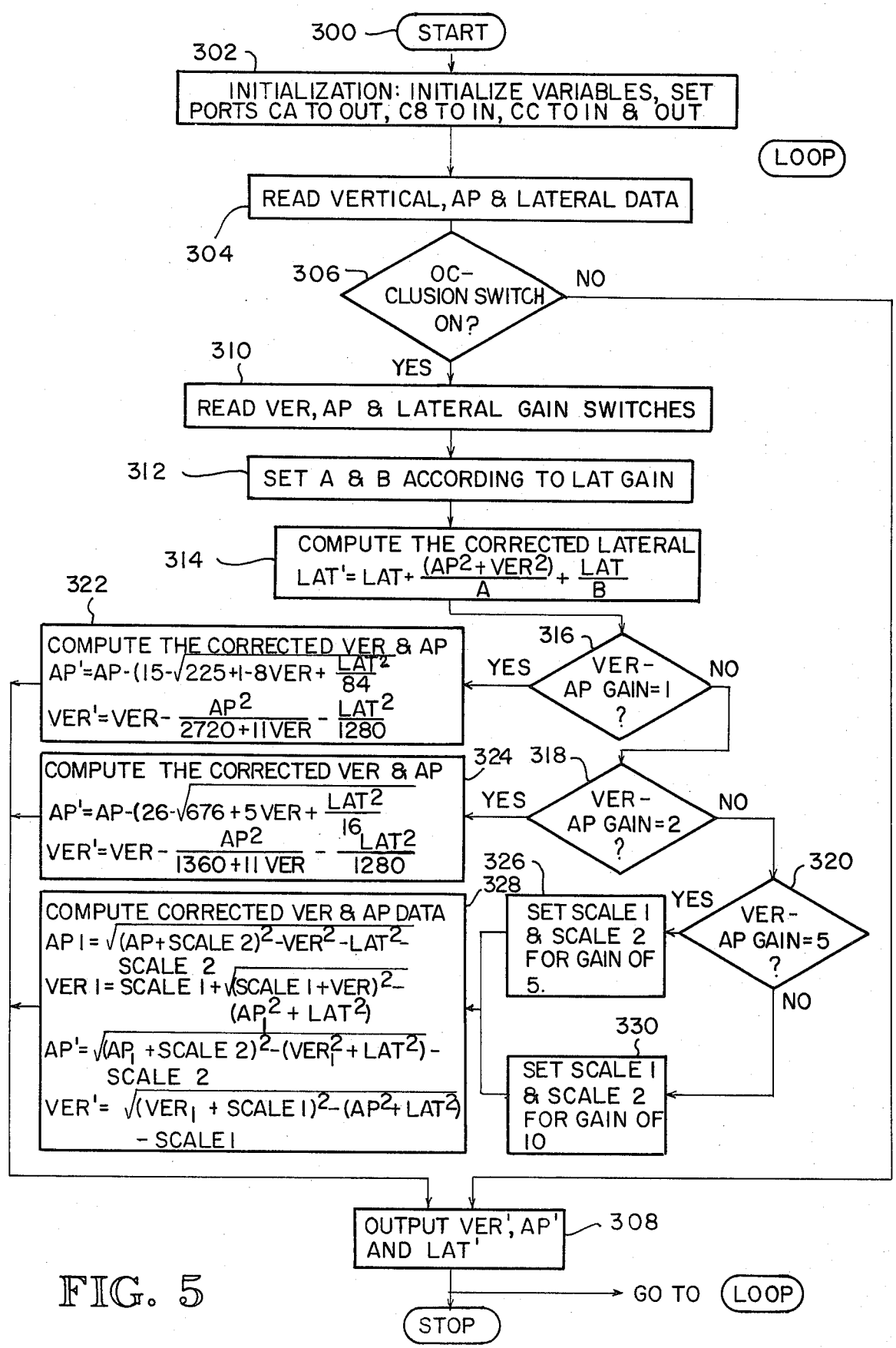
FIG. 5 is a flow chart of the program instructions for the processing unit.

A flow chart of the program instructions for the processing unit 58 is illustrated in FIG. 5. When the reset switch 32B is closed, the processing unit 58 is reset and the program jumps to the start instruction 300. Initialization then takes place at 302, in which the variables in the program are initialized and the microprocessor is connected to various input and output ports. Data corresponding to the VER, A/P and LAT variables are read at 304, and the occlusion switch 32A is examined at 306. If the occlusion switch is not closed, the program branches to 308, in which the coordinates representing the actual position of the magnet are presented to the output ports of the processing unit 58. The program then returns to the block 304, and the occlusion switch 32A is then continuously scanned in like manner. When the occlusion switch 32A is finally closed, the program branches to 310, where the gain controls 26-30 for the vertical, anterior-posterior, vertical velocity and lateral inputs are read. Program variables are set to the lateral gain at 312 and the actual lateral position LAT' is calculated at 314 in accordance with the formula given therein. After the coordinates representing the actual lateral position of the magnet have been calculated, the program steps to 316, where the program branches, depending upon whether the VER- A/P gain is equal to "1." If the gain is not equal to "1," the program branches to 318 and the gain control 26 is examined to determine whether the gain is "2." If the gain is not equal to "2," the program branches to 320, where it is determined whether the gain is equal to "5."

If the VER-A/P gain has been found to be "1" at 316, the actual anterior-posterior A/P' and actual vertical position VER' are calculated at 322 in accordance with the formula given therein. If the VER-A/P gain is "2," the A/P' and VER' coordinates are calculated at 324 in accordance with the formula given therein. If the VER-A/P is "5," SCALE 1 and SCALE 2 are set for a gain of "5" at 326, and the A/P' and VER' coordinates are calculated at 328 in accordance with the formula given therein. If the VER-A/P gain is not "5," then it must be "10." Accordingly, the SCALE 1 and SCALE 2 variables are set for a gain of "10" at 330, and the actual position coordinates are calculated with the formula in 328. The program then branches to 308, where the output coordinates VER', A/P' and LAT' are presented to the output ports of the processing unit 58. The program then normally loops back to 304, where the above-described procedure is repeated.

The hex codes for programming a microprocessor in accordance with the flow chart of FIG. 5 are as follows:

```
:02000002FF807D
:02000000FFFF00
:02000002FFE21B
:100002005598EC8B4E0E4099F77E0489064A028B93
:100012004606880E4A0299F7F92BC1BB020099F7EB
:100022000FB03C1890640023BC17D03E90300E90BD6
:1000320000B8B064C028390640A02E9D3FF8B064C0026A
:0400420050C2040097
:02000002FF807D
```

```
:10000200FA2E8E160000BC1A048BEC161FFBC606D5
:100012005102000606520200B098E6CEB007E6CC06
:10002200B009E6CCC606530200803E530280720833A
:10003200E90900E4CC880653022E9EDFFE4C8F6D8EA
:100042008B064E02B000E6CCB002E6CCB00AE6CC9E
:10005200C60653020080E53028072003E90900E49F
:10006200CC880653022E9EDFFE4C8F6D888064F02B1
:10007200B000E6CCB003E6CCB00BE6CCC606530229
:100082000080E53028072003E90900E4CC880653E3
:1000920002E9EDFFE4C8F6D888065002B007E6CCC4
:1000A2008A064E02B400B9800002BC189062A028A50
:1000B200064F02B4002BC189062C028A065002B4F4
:1000C200002BC189062E02B000E6CCE4CC88065192
:1000D2002803E510270B0FF76014050803E5102D4
:1000E20040B0FF7301405922C1D0D87203E9140114
:1000F2008B062A028906340288062C028906362F6
:100102008B062E028906380280002E6CCE4CC8806C1
:10011200510280F8727403E90C00C70646022C01F2
:10012200C706480258028003E510262 7403E90C007D
:10013200C706460220C01C706480229600803E5102BD
:10014200527403E90C00C706460 26E00C706480255
:100152004000803E5102427403E90C00C706460 289
:100162006E00C70648 0 21000B000E6CCB002B178BB
:10017200D2E9FEC875F8E4CC880651028 0F87074A2
:1001820003E90B00C70628020500C606520 20180D9
:1001920003E5102607403E90B00C70628020600C63E
:1001A2000065202028003E5102507403E92300C70640
:1001B2001E02020 0C70620 0204 00C7062202ECFF4C
:1001C200C7064202BD00C706440 26000C606520 2CC
:1001D2005803E5102407403E92300C7061E020255
:1001E2000000C706 200204 00C7062202F1FFC706422A
:1001F200025E00C7064402 3000C60652020AE90344
:100202000000E9CDFEB007E6CC823E52020 7403E95B
:10021200030 0E9C8038B06340229062A028B06363C
:100222000229062C028B063802290 62E028 03E5233
:100232000 2017503E90A008 03E52020 27403E90 3D7
:100242000 00E90300E965018B062A02B9 020099F769
:10025200F989062A028B062C0299F7F989062C02E3
:10026200F7E8508B062A02F7E85903C199F73E4690
:100272000028 9061202F72E20299F73E48028BBED1
:100282002E0203C189061002803E52020 17403E964
:10029200680 08B062A02BA10 00F7EAB80 90099F738
:1002A200FB81C0E10050 89C8F7E8B9540099F7F919
:1002B2005903C189061402 50FF362802E86103B9C6
:1002C2000F002BC8290E2C028B062C02F7E8508B4C
:1002D20062A02B90B00F7E981C0A0 0A89C1589920
:1002E200F7F98B0E2A022BC88B062E02F7E8BB0009
:1002F2000A99F7FB2BC8890E2A02803E52020 27429
:100302000 03E9640 08B062A02B90500F7E981C0A45B
:1003120002508B062E02F7E8B9100099F7F959033B
:10032200C189061402 50FF362802E8F302B91A0006
:100332002BC8290E2C028B062C02F7E8508B062ABA
:100342002B90B00F7E981C0500589C15899F7F944
:100352008B0E2A022BC88B062E02F7E8BB000599EA
:10036200F7FB2BC8890E2A028B062A02B90200F774
:100372000 0E989062A028B062C02F7E989062C028BF0
```

```
:1003820006340203062A02F7D8890618028B0636BB
:100392000203062C02F7D889061C028B06380203D8
:1003A200062E02F7D8890610002E9AA01C70628021A
:1003B2001E00813E2C02A4007F03E90300E996019E
:1003C2008B062A023B0622027F03E92E008B0E34A3
:1003D2000203C8F7D9890E18028B06360203062CCF
:1003E20002F7D889061C028B06380203062E02F792
:0F03F200D889061002E95E01E9C5FF8B062A02D1
:02000002FFC03D
:100001008B0E1E0231D2F7F9891626028B062A02BF
:1000110099F7F989062A02F7E889063A028B06421E
:100021000203062A02F7E889063C028B062C0231FC
:100031000D2F7F9891624028B062C0299F7F9890661
:100041002C028B0E440203C889C8F7E889063E02D8
:100051008B062C02F7E803063A0299F73E4602891D
:10006100061202B9C18B062E02F7E999F73E480272
:100071003062E02B90610002F7E899F73E2002894D
:1000810006400208B063E022B063A022B06400289ED
:1000910006140250FF362802E886012B0644028925
:1000A100061A028B061A02F7E88B0E3C022BC82BAC
:1000B1000E4002890E14028B164202F7DA5251FFEA
:1000C100362802E85B015903C1890616028B061620
:1000D10002F7E88B0E3E022BC82B0E4002890E144C
:1000E100251FF362802E838012B06440289061C1A
:1000F100028B061C02F7E88B0E3C022BC82B0E402C
:100101002890E14028B164202F7DA5251FF362889
:100111002E80D015903C1890618028B0E3402F75A
:10012100D98B061802F72E1E022BC8030E26028950
:10013100E18028B061E02F7D8F72E1C022B06247E
:10014100022B06360289061C028B061002F7D82BF9
:1001510063802890610028533E18020070C3E90D6D
:1001610008B061802F6D080C08088064E02833EBE
:100171001802007D03E90C008B061802B1802AC821
:1001810088E4E02833E1C020070C3E90D008B06A3
:100191001C02F6D080C08088064F02833E1C0200FC
:1001A1007D03E90C008B061C02B1802AC8880E4F22
:1001B100028B3E10020070C3E90D008B061002F65B
:1001C100D080C080880650028533E10020070D3E982
:1001D100C008B061002B1802AC8880E50028A06D4
:1001E1004E02E6CAB007E6CCB00FE6CCB007E6CCCB
:1001F100B004E6CC8A064F02E6CAB007E6CCB00FDF
:100201000E6CCB005E6CC8A065002E6CAB007E6CCD9
:100211000B00FE6CCB007E6CCB006E6CCE9FEF9FBC0
:01022100F4E8
:02000002FFFFFE
:050000000EA020080FF90
:04000003FF80000278
:00000001FF
```

It will be understood by one skilled in the art that each instruction consists of four hexi-decimal characters, although all such codes are grouped together above.

It is thus seen that the compensating system generates corrected position signals which may be used by the kinesiograph mandibular tracker in the same manner as the uncorrected position signals, thus making significant modification of the kinesiograph mandibular tracker unnecessary. Furthermore, the inherent symmetry of operation of the compensating system ensures that the corrected position signals correspond to the position coordinate of the corresponding uncorrected position signal. Although the system has been described for use with a kinesiograph mandibular tracker which tracks the movement of a magnet, it will be understood that geometric distortions occur anytime a reference point is not moving toward or away from a sensor which measures the distance between the sensor and the reference point.

I claim:

1. In a kinesiograph mandibular tracker for measuring mandibular movements in at least one plane, said kinesiograph mandibular tracker including an array of sensors each of which generates an output signal representing the distance between a reference point on a patient's mandible and that sensor, said kinesiograph mandibular tracker generating from said sensor output signals, position signals which correspond to the approximate position coordinates of said reference point in said plane, a system for compensating for geometric distortions inherent in said kinesiograph mandibular tracker, comprising:

first sample-and-hold means for periodically sampling said position signals and storing signals representative thereof;

second means for calculating from said storage samples, position coordinates corresponding to the actual position of said reference point within said plane using the same coordinate system as said approximate position coordinates; and third means for generating respective corrected position signals which correspond to said actual position coordinates so that said corrected position signals may be applied to said kinesiograph mandibular tracker in the same manner that corresponding position signals are applied to said kinesiograph mandibular tracker, whereby said kinesiograph mandibular tracker can display the actual position of said reference point without significant internal modification.

2. The compensating system of claim 1 wherein said second means comprise:

first multiplexer means for sequentially selecting and isolating each of said storage samples one at a time;

analog-to-digital convertor means for generating a digital word representative of the sample selected and isolated by said first multiplexer means; and processing means for sequentially storing the digital word for each of said samples, calculating from said digital words said actual position coordinates, and sequentially generating respective digital words representative of said actual position coordinates.

3. The compensating system of claim 2 wherein said third means comprise:

digital-to-analog convertor means for sequentially receiving the digital words from said calculator means one at a time and for generating analog signals corresponding thereto;

second multiplexer means for applying said analog signals to one of a plurality of output lines depending upon which position coordinate said analog signal represents; and second sample-and-hold means for periodically sampling the output lines of second multiplexer means, storing said samples and continuously generating as said corrected position signals, respective output signals representative of said actual position coordinates which may be applied to said kinesiograph mandibular tracker in the same manner that corresponding approximate position signals are applied to said kinesiograph mandibular tracker.

4. The compensating system of claim 3 wherein said first and second multiplexer means are operated by common control signals so that maximum utilization of a limited number of control lines is achieved.

5. The compensating system of claim 4 wherein said first and second sample-and-hold means are operated by common control signals, and said analog-to-digital convertor means and digital-to-analog convertor means are operated by common control signals so that maximum utilization of a limited number of control lines is achieved.

6. The compensating system of claim 3, further including respective high-pass filter means connected to the output lines of said second sample-and-hold means for attenuating frequency components of said actual position signals higher than a predetermined value.

7. The compensating system of claim 3, further including notch filter means connected to the output lines of said second sample-and-hold means for attenuating a predetermined frequency component of said actual position signals.

8. The compensating system of claim 1, further including means for differentiating one of said corrected position signals to allow said kinesiograph mandibular tracker to display the velocity of said reference point.

9. A kinesiograph mandibular tracker for measuring mandibular movement, comprising:

an array of non-coplanar sensors generating respective output signals corresponding to the signals between said sensors and a reference point on a patient's mandible;

means receiving said sensor output signals for generating from said output signals vertical, anterior-posterior and lateral position signals corresponding, respectively, to the approximate position of said reference point in vertical, anterior-posterior and lateral directions;

first sample-and-hold means for periodically sampling said vertical, anterior-posterior and lateral position signals and storing signals representative thereof;

first multiplexer means for sequentially selecting and isolating each of said storage samples one at a time;

analog-to-digital convertor means for generating a digital word representative of the sample selected and isolated by said first multiplexer means;

processing means for sequentially storing the digital word for each of said samples, calculating from said digital word the actual vertical, anterior-posterior and lateral position of said reference point, and sequentially generating respective digital words representative of said actual position;

digital-to-analog convertor means sequentially receiving the digital words from said processing means one at a time and for generating analog signals corresponding thereto;

second multiplexer means for applying said analog signals to one of a plurality of output lines depending upon which position coordinate said analog signal represents;

second sample and hold means for periodically sampling the output lines of said second multiplexer means, storing said samples, and continuously generating corrected vertical, anterior-posterior and lateral position signals representative of the actual vertical, anterior-posterior and lateral position, respectively, of said reference point; and means for displaying said corrected vertical, anterior-posterior and lateral position signals.

10. The compensating system of claim 9 wherein said first and second multiplexer means are operated by common control signals so that maximum utilization of a limited number of control lines is achieved.

11. The compensating system of claim 10 wherein said first and second sample-and-hold means are operated by common control signals, and said analog-to-digital convertor means and said digital-to-analog convertor means are operated by common control signals so that selection of an approximate position coordinate for processing by said processing means is synchronized with the routing of an actual position coordinate to an output line of said second sample-and-hold means corresponding to the selected approximate position coordinate.

12. In a kinesiograph mandibular tracker for measuring mandibular movements in at least one plane, said kinesiograph mandibular tracker including an array of sensors generating respective output signals representing the distance between a reference point on a patient's mandible and each of said sensors, said kinesiograph mandibular tracker generating from said sensor output signals, position signals which correspond to the approximate position coordinates of said reference point in said plane, a system for compensating for geometric distortions in said kinesiograph mandibular tracker, comprising:

first means for digitizing said approximate position signals, thereby generating digital words indicative of the approximate position coordinates of said reference point;

second means for calculating from said digital words the actual position of said reference point and for generating respective digital words representing the actual position coordinates of said reference point using the same coordinate system as said approximate position coordinates; and third means for converting digital words corresponding to the actual position coordinates to respective analog actual position signals so that said actual position signals may be applied to said kinesiograph mandibular tracker in the same manner that corresponding approximate position signals are applied to said kinesiograph mandibular tracker.

* * * * *